United States Patent [19]

Yatagai et al.

[11] Patent Number: 4,973,689
[45] Date of Patent: Nov. 27, 1990

[54] METHOD FOR PRODUCTION OF CYCLOHEXANECARBOGUANAMINE

[75] Inventors: Hidetaka Yatagai, Nishinomiya; Osamu Kaieda, Tsukuba; Jiro Iriguchi, Takatsuki; Souichi Yamada, Kyoto; Tsuguo Takaya, Otsu, all of Japan

[73] Assignee: Nippon Shokubai Kagaku Kogyo Co., Ltd., Osaka, Japan

[21] Appl. No.: 279,938

[22] Filed: Dec. 5, 1988

[30] Foreign Application Priority Data

Dec. 11, 1987 [JP] Japan ................. 62-312336
Dec. 15, 1987 [JP] Japan ................. 62-315118

[51] Int. Cl.$^5$ .......................................... C07D 251/18
[52] U.S. Cl. ................................................ 544/206
[58] Field of Search ........................................ 544/206

[56] References Cited

U.S. PATENT DOCUMENTS 2,606,904  8/1952  Kaiser ........................... 260/249.9
3,379,661  4/1968  Gynn et al. ..................... 260/17.3
4,673,757  6/1987  Fiedler et al. .................... 558/431

FOREIGN PATENT DOCUMENTS 1390116   1/1965   France .
38/8328   6/1963   Japan .
38/8329   6/1963   Japan .
40/2353   2/1965   Japan .
40/22190 10/1965   Japan .
50/1034   1/1975   Japan .

Primary Examiner—John M. Ford
Attorney, Agent, or Firm—Burns, Doane, Swecker & Mathis

[57] ABSTRACT

In a method for the production of cyclohexanecarboguanamine by the reaction of cyanocyclohexane with dicyandiamide in an organic solvent possessing a hydroxyl group in the molecular unit thereof at a temperature in the range of 90° to 200° C. in the presence of a basic catalyst, the improvement which comprises carrying out the reaction using 0.60 to 0.95 mol of dicyandiamide per mol of cyanocyclohexane in an atmosphere substantially incapable of producing any effect of oxygen.

9 Claims, No Drawings

METHOD FOR PRODUCTION OF CYCLOHEXANECARBOGUANAMINE

BACKGROUND OF THE INVENTION

1. Field of the Invention

This invention relates to a method for the production of cyclohexanecarboguanamine. More particularly, it relates to a method for the production of cyclohexanecarboguanamine represented by the following formula I, which is useful as a resin material for molding materials, laminate sheet materials, and vehicles in coating materials and as a starting material for resin modifiers and medicines:

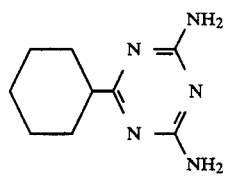

2. Description of the Prior Art

A method for the synthesis of guanamine compounds by the thermal reaction of fatty acid nitriles with dicyandiamide has been widely known to the art [Smolin and Rapoport: "The Chemistry of Heterocyclic Compounds (s-Triazine and Derivatives)," 1959, page 229, Interscience Publishers Inc. and Japanese Patent Publication SHO Nos. 40(1965)-2,353 and 40(1965)-22,190, etc.].

A method for the synthesis of cyclohexanecarboguanamine is disclosed in U.S. Pat. No. 3,379,661. In Example 1 cited in the specification of this U.S. patent, it is stated that cyclohexanecarboguanamine was obtained by placing cyanocylohexane and dicyandiamide in ethylene glycol monomethyl ether solvent and boiling the solvent in the presence of a potassium hydroxide catalyst thereby effecting a reaction. The method disclosed in the U.S. patent is based on the well-known method for the production of guanamine compounds.

We have found that the cyclohexanecarboguanamine obtained by the conventional method available for the production of guanamines is colored and must be purified into a white product of high quality to be used satisfactorily as a material for various resin products, as a resin modifier, or as a starting material for medicines. A method for the purificaiton of guanamine compounds is disclosed in Japanese Patent Publication SHO No. 38(1963)-8,328 and SHO No. 38(1963)-8,329, for example. By this method, white guanamines are obtained by purifying guanamine compounds by means of recrystalization or sublimation. This method, therefore, involves many steps of operation and proves to be a process of poor economy.

In U.S. Pat. No. 3,379,661, there is no mention of the yield of production. We tried to synthesize cyclohexanecarboguanamine in accordance with the method disclosed in the U.S. patent and obtained the compound only in low yield (as demonstrated in Control 2 cited thereinafter).

As a method for the production of cyclohexanecarboguanamine, the present invention contemplates a method of sequentially adding dicyandiamide to a solvent containing cyanocyclohexane. There have existed similar methods which synthesize guanamine compounds from fatty acid nitriles by sequential addition of dicyandiamide in French Patent No. 1,390,116 and U.S. Pat. No. 2,606,904, for example. According to the French Patent, a sulfoxide such as dimethyl sulfoxide is used as a solvent and dicyandiamide is added over a period of at least one hour to a fatty acid nitriles dissolved in advance in the solvent. The French patent mentioned above does not teach any method using cyanocyclohexane as a fatty acid nitrile.

We followed a specific method disclosed in the French patent to try synthesis of cyclohexanecarboguanamine using cyanocyclohexane as a cyan compound and obtained the compound only in low yield. All these results imply that the method of the French Patent resorting to sequential addition and using sulfoxide as a solvent is not always suitable for the reaction under discussion.

In accordance with the method disclosed in U.S. Pat. No. 2,606,904, it is stated that, in the reaction of dicyandiamide with a higher fatty acid nitrile possessing an alkyl or alkenyl group of not less than 8 carbon atoms, sequential addition of the dicyandiamide results in the production of a corresponding guanamine in a yield in the range of 60 to 70%. This yield of the reaction, however, is not sufficient for the method to be fully feasible from the commercial point of view.

In the conventional method for synthesizing a guanamine compound from a fatty acid nitrile and dicyandiamide, it is normal to use the dicyandiamide in a ratio of not less than one mole per mole of the fatty acid nitrile.

Other methods for the synthesis of cyanocyclohexane, a starting material for the method of the present invention, are disclosed in U.S. Pat. No. 3,379,661, Japanese Patent Publication SHO No. 50(1975)-1,034, and U.S. Pat. No. 4,673,757. The method of U.S. Pat. No. 3,379,661 comprises hydrogenating cyanocyclohexene under a pressure of 1,000 lb/in$^2$ (equal to about 70.3 kg/cm$^2$) in the presence of a palladium catalyst supported on carbon thereby effecting synthesis of cyanocyclohexane. This U.S. patent has absolutely no disclosure about such reaction conditions as reaction temperature and amount of catalyst. The disclosure only goes to the length of suggesting the possibility of the reaction. Absolutely no mention is made of the quality of the produced cyanocylohexane anywhere in the specification thereof. Further, this method has a disadvantage that the reaction pressure is so high as to require use of an expensive apparatus. The method disclosed in Japanese Patent Publication SHO No. 50(1975)-1,034 comprises subjecting 4-cyanocyclohexene to hydrogenation at a temperature in the range of 100° to 110° C. under a pressure of 80 to 100 atmospheres in the presence of a rhodium trichloride catalyst thereby producing cyanocyclohexane. This method similarly has a disadvantage that the reaction pressure is so high as to require use of an expensive apparatus. It also requires use of an expensive catalyst and does not fit commercialization. The method disclosed in U.S. Pat. No. 4,673,757 comprises hydrogenating cyanocyclohexene at a temperature of 120° C. in the presence of a ruthenium-triphenyl phosphine catalyst thereby producing cyanocyclohexane. This method is similarly unfit for commercialization because it requires use of an expensive catalyst.

An object of this invention is to provide a method for the production of cyclohexanecarboguanamine of high purity.

Another object of this invention is to provide an economically advantageous method for commercial production of uncolored white cyclohexanecarboguanamine of high quality in high yield enough to be used as a starting material for various resin materials, resin modifier, and medicines.

Yet another object of this invention is to provide an economically advantageous method for commercial production of cyanocyclohexane of high quality in high yield enough to be used as a raw material for the synthesis of the cyclohexanecarboguanamine mentioned above.

SUMMARY OF THE INVENTION

These objects are accomplished by a method for the production of cyclohexanecarboguanamine by the reaction of cyanocyclohexane with dicyandiamide in an organic solvent having a hydroxyl group in the molecular unit thereof at a temperature in the range of 90° to 200° C. in the presence of a basic catalyst, which comprises carrying out the reaction using the dicyandiamide in a ratio in the range of 0.6 to 0.95 mol per mol of the cyanocyclohexane in an atmosphere substantially incapable of producing any effect of oxygen.

These objects are also accomplished by a method for the production of cyanocyclohexane by the hydrogenation of cyanocyclohexene at a temperature in the range of 0° to 100° C. under a hydrogen pressure in the range of 2 to 20 kg/cm² in the presence of 0.0005 to 0.05% by weight of a metallic palladium catalyst, based on the amount of the cyanocyclohexene.

EXPLANATION OF PREFERRED EMBODIMENT

The atmosphere substantially incapable of producing any effect of oxygen as contemplated by the present invention is preferable to be the atmosphere of at least one inert gas selected from the group consisting of nitrogen and argon. As means of establishing the atmosphere substantially incapable of producing any effect of oxygen, a method which comprises displacing the interior of a given reaction system with an inert gas in advance, a method which comprises continuing the reaction while keeping supply of an inert gas into the reaction system, and a method which comprises displacing the interior of the reaction system several times with an inert gas and then continuing the reaction while keeping supply of an inert gas into the reaction system. In the present reaction, the color assumed by the produced cyclohexanecarboguanamine gains in density in proportion as the oxygen concentration in the atmosphere increases. Thus, this reaction is generally carried out in such a manner that the oxygen concentration in the atmosphere remains below 5% by volume, preferably below 2.5% by volume.

In the present invention, cyclohexanecarboguanamine represented by the following formula I:

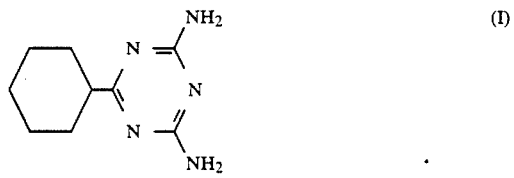

is produced by using 0.60 to 0.95 mol, preferably 0.65 to 0.90 mol, of dicyandiamide per mol of cyanocyclohexane. This particular ratio is necessary for the purpose of curbing by-production of melamine due to self-condensation of dicyandiamide, heightening the yeild of the reaction and, at the same time, ensuring production of cyclohexanecarboguanamide of high quality having a very small melamine content. The effect of this curbing increases in proportion as the ratio of dicyandiamide to cyanocyclohexane decreases. If the amount of dicyandiamide is less than 0.60 mol, the reaction is deficient in productivity. If the amount exceeds 0.95 mol, the effect of curbing is short of being satisfactory. This effect of curbing is further enhanced by using sequential addition of dicyandiamide for the reaction. Generally, it is desirable to effect this sequential addition of dicyandiamide at a speed in the range of 0.05 to 0.35 mol per hour per mol of cyanocyclohexane. If the sequential addition is made at a speed higher than the upper limit of the range, the effect of curbing the by-production of melamin is insufficient. If it is made at a speed lower than the lower limit, the reaction time is unduly long and the reaction is deficient in productivity. In the sequential addition of dicyandiamide, the dicyandimide can be used as a solid form. The addition, however, can be obtained easily by using dicyandiamide as suspended and/or dissolved in the same organic solvent as used in the reaction. In this case, it has no objection that the cyanocyclohexane, being the raw material, is incorporated in the solvent.

In the present invention, since cyanocyclohexane is used in an excess amount relative to dicyandiamide, the reaction solution obtained at the end of the reaction contains unaltered cyanocyclohexane. This unaltered cyanocyclohexane can be easily recovered from the reaction solution as by distillation. The recovered unaltered cyanocyclohexane can be recycled for re-use in the next cycle of the reaction. Though the distillation of the reaction solution for the recovery of the unaltered cyanocyclohexane may be effected under normal pressure, it is desired to be carried out under reduced pressure.

As described above, the present invention enables the yeild of cyclohexanecarboguanamine based on dicyandiamide to be enhanced by curbing the by-production of melamine due to self-condensation of dicyandiamide and also enables the yield of cyclohexanecarboguanamide based on cyanocyclohexane by ensuring effective recovery and re-use of the unaltered cyanocyclohexane.

We have made a study further on cyanocyclohexane as a starting material for the purpose of producing cyclohexanecarboguanamine of high quality free from coloration. We have found consequently that the amount of catalyst, the reaction temperature, and hydrogen pressure to be used in the production of cyanocyclohexane by the hydrogenation of cyanocyclohexene are important factors for the production of colorless cyclohexanecarboguanamine. To be specific, the hydrogenation is preferable to be carried out by using metallic palladium as a catalyst in an amount in the range of 0.0005 to 0.05% by weight, preferably 0.001 to 0.045% by weight, based on the charged amount of cyanocyclohexene at a reaction temperature in the range of 0° to 100° C., preferably 20° to 80° C., under a hydrogen pressure in the range of 2 to 20 kg/cm², preferably 2 to 15 kg/cm². If the amount of the catalyst is larger than its upper limit, the reaction temperature higher than its upper limit, or the hydrogen pressure higher than its upper limit or lower than its lower limit, the reaction tends to entail occurrence of a by-product responsible for coloration of cyclohexanecarboguanamine and, consequently, necessitate use of devices of distillation and purification for the removal of the by-product from the reaction solution. If the amount of the catalyst is smaller than its lower limit or the reaction temperature is lower than its lower limit, there ensues a disadvantage that the reaction proceeds slowly and suffers from a decline in productivity. The catalyst may be used in a form having the activity thereof enhanced in advance by a heat treatment carried out under hydrogen pressure. The cyanocyclohexane obtained by the catalytic hydrogenation of cyanocyclohexene under reaction conditions described above may be deprived of the used catalyst by a simple measure such as filtration and may be used as a raw material for cyclohexanecarboguanamine without going through any additional step of purification as by distillation. To be used as the catalyst, the metallic palladium is generally used in a form supported on carbon.

The organic solvent possessing a hydroxyl group in the molecular unit thereof and used in the production of cyclohexanecarboguanamine by the reaction of cyanocyclohexane with dicyandiamide is desired to be at least one compound selected from the group consisting of ethylene glycol monoalkyl ethers represented by the following formula II:

ROCH$_2$CH$_2$OH    (II)

wherein R is an alkyl group of 1 to 4 carbon atoms, and butanols. The ethylene glycol monoalkyl ethers usable herein include ethylene glycol monomethyl ether, ethylene glycol monoethyl ether, ethylene glycol monoisopropyl ether, and ethylene glycol monobutyl ether, for example. The butanols usable herein include n-butanol, isobutanol, sec-butanol, and t-butanol, for example.

The reaction temperature is preferable to be in the range of 90° to 200° C., preferably 110° to 180° C. If the reaction temperature is unduly high, the reaction is liable to entail by-production of melamine due to self condensation of dicyandiamide. Conversely, if the reaction temperature is unduly low, there arises a disadvantage that the reaction velocity is low and the reaction suffers from inferior productivity. The basic catalyst to be used in the reaction is not specifically defined. It is generally selected from the group consisting of alkali metal hydroxides such as potassium hydroxide, sodium hydroxide, and lithium hydroxide and alkali metal alcoholates such as potassium methoxide, sodium methoxide, and sodium ethoxide. Generally, the amount of the basic catalyst to be used is approximately in the range of 0.5 to 20 mol% based on the charged amount of cyanocyclohexane.

The cyanocyclohexene to be used in the present invention as a raw material for cyanocyclohexane is not specifically defined. The 4-cyanocyclohexene which is obtained by the Diels-Alder reaction of butadiene with acrylonitrile is easy to procure as a raw material and also easy to handle in the intended production of cyanocyclohexane and, therefore, is easily utilized from the commercial point of view.

Since the method of this invention is capable of synthesizing highly pure white cyclohexanecarboguanamine having a small content of by-produced melamine, it permits production of a colorless highly pure finished product through a simple step of washing with water for the removal of the basic catalyst and a small amount of by-produced melamine without requiring any step of purification as by recrystallization. Thus, the method of the present invention is commercially advantageous for the production of cyclohexanecarboguanamine.

Now, the present invention will be described more specifically below with reference to working examples. It should be noted that this invention is not limited in any way by these working examples.

In the following examples, the analysis of various compounds, the analysis of the gas in the reaction vessel for oxygen concentration, and the evaluation of the degree of coloration of cyclohexanecarboguanamine were carried out as follows.

(1) The content of cyanocyclohexane was determined by gas chromatography and the contents of melamine, dicyandiamide, and cyclohexanecarboguanamine were determined by HPLC.

(2) The oxygen concentration of the gas inside the reaction vessel was determined by gas chromatography (Detector: TCD).

(3) The degree of coloration of cyclohexanecarboguanamine was evaluated in terms of the Hasen color number obtained of a methylolated resin made of a given sample by the following procedure: An eggplant-shaped flask having an inner volume of 200 ml was charged with 10g of cyclohexanecarboguanamine, 13 g of an aqueous 37% by weight formalin solution, and 0.1 g of an aqueous 5% by weight sodium carbonate solution, set in place in a rotary evaporator, and then rotated and heated to 90° C. When the cyclohexanecarboguanamine was dissolved and the reaction solution was homogenized, the reaction system was vacuumized to 50 mmHg to expel water and unaltered formaldehyde. When the amount of the mixed liquid of water and unaltered formaldehyde resulting from distillation increased to about 8 g, the methylolated resin remaining in the flask was transferred into a test tube and, in its molten state (50° to 70° C.), was compared with Hasen color number standard solutions to find the Hasen color number.

PRODUCTION EXAMPLE 1

A stainless steel autoclave having an inner volume of 2 liters was charged with 1,200 g of 4-cyanocyclohexene and 1.20 g of palladium carbon on which 5% by weight of palladium was supported (containing 0.005% by weight of palladium, based on the amount of 4-cyanocyclohexene) and, with the interior gas of the autoclave displaced with hydrogen, charged with hydrogen up to 10 kg/cm$^2$. The resultant mixture was stirred and heated to 70° C. In the meanwhile, the reaction mixture was replenished with hydrogen to keep the interior of the autoclave at a hydrogen pressure of 10 kg/cm$^2$. The reaction was further continued at 70° C. under 10 kg/cm$^2$ until the absorption of hydrogen ceased to exist. Then, the reaction solution was cooled to normal room temperature and then removed from the autoclave. The reaction solution was passed through a membrane filter to remove the palladium carbon and obtain 1221 g of cyanocyclohexane (A).

PRODUCTION EXAMPLES 2–7

Cyanocyclohexane (B) to (G) were obtained by following the procedure of Production Example 1, except that the amount of palladium carbon to be used, the hydrogen pressure, and the reaction temperature were changed as indicated in Table 1.

PRODUCTION EXAMPLE 8

By distilling 850 g of cyanocyclohexane (G) under a vacuum, there was obtained as a fraction of distillation 700 g of cyanocyclohexane (M) having a boiling point in the range of 110° to 112° C./90 mmHg.

TABLE 1

| Production Example | Cyano-cyclo-hexane | Palladium carbon Weight (g) | wt %[1] | Reaction temperature (°C.) | Hydrogen pressure (kg/cm$^2$) |
|---|---|---|---|---|---|
| 1 | A | 1.20 | 0.005 | 70 | 10 |
| 2 | B | 1.20 | 0.005 | 70 | 3 |
| 3 | C | 1.20 | 0.005 | 70 | 1.5 |
| 4 | D | 2.40 | 0.010 | 70 | 10 |
| 5 | E | 0.60 | 0.0025 | 70 | 10 |
| 6 | F | 24.0 | 0.10 | 70 | 10 |
| 7 | G | 2.40 | 0.005 | 130 | 10 |

[1] Ratio of metallic palladium, in % by weight, based on cyanocyclohexene.

EXAMPLE 1

A four-necked flask having an inner volume of 2 liters was fitted with a thermometer, a stirrer, and a reflux condenser, with one remaining port connected to a tube pump. After the interior of the flask was displaced with nitrogen, the flask was charged with 300 g of ethylene glycol monomethyl ether, 350 g (3.21 mols) of cyanocyclohexane (A), and 9.0 g (0.16 mol) of potassium hydroxide. The contents of the flask were stirred, with the interior thereof displaced several times with nitrogen. After the oxygen concentration of the gas in the flask was confirmed to be not more than 2.5% by volume, the flow of nitrogen to the flask interior was continued to keep the oxygen concentration of the internal gas of the flask below 2.5% by volume and the contents of the flask were stirred and heated to a reflux level. After the reflux started, 243 g of dicyandiamide (2.89 mols; 0.90 mol part per mol part of the charged cyanocyclohexane) was added at a fixed speed (0.2 mol part per hour per 1 mol part of the charged cyanocyclohexane) to the flask over a period of 4.5 hours by a procedure which comprised suspending the dicyandiamide in the expelled distillate, and returning the suspension into the flask by the tube pump. After completion of this addition of the dicyandiamide, the contents of the flask were stirred further for one hour under the reflux conditions and then cooled to 100° C. After the cooling, the reaction mixture was transferred into a kneader having an inner volume of 2 liters and then heated under a vacuum (50 to 500 mmHg) to recover a mixture of 297 g of ethylene glycol monomethyl ether and 54 g of unaltered cyanocyclohexane. The light yellow solid substance consequently obtained and 690 ml of water added thereto were heated and stirred at 90° C. The resultant mixture was filtered and the solid substance produced by filtration was dried. Consequently, there was obtained 519 g of cyclohexanecarboguanamine (2.69 mols) possessing purity of 99.9% by weight. The yield of this reaction and the Hasen color number of methylolated resin were as shown in Table 2.

EXAMPLE 2

In the same reactor as used in Example 1, with the inner gas thereof displaced with nitrogen, 350 g of cyanocyclohexane (B), 50 g of ethylene glycol monomethyl ether, and 9.0 g of potassium hydroxide were placed and stirred. In the meantime, the interior of the reactor was displaced several times with nitrogen. After the oxygen concentration in the inner gas of the reactor was confirmed to be not more than 2.5% by volume, the flow of nitrogen to the reactor interior was continued to keep the oxygen concentration of the inner gas of the reactor below 2.5% by volume and the contents of the reactor were stirred and heated to 130° C. After the temperature of the reaction mixture in the vessel reached 130° C., a mixed slurry comprising 250 g of ethylene glycol monomethyl ether and 243 g of dicyandiamide (0.9 mol part per mol part of the charged cyanocyclohexane) was added at a fixed speed through the tube pump to the reactor interior (0.2 mol part per hour per mol part of the cyanocyclohexane) over a period of 4.5 hours. After the addition, the resultant mixture was further stirred at 130° C. for one hour and then cooled to 100° C. Thereafter, the reaction mixture was treated by following the procedure of Example 1. Consequently, a mixture comprising 298 g of ethylene glycol monomethyl ether and 53 g of unaltered cyanocylohexane was recovered and 520 g (2.69 mols of cyclohexanecarboguanamine having a purity of 99.9% by weight was obtained. The yield of the reaction and the Hasen color number of the methylolated resin were as shown in Table 2.

EXAMPLE 3

The procedure of Example 1 was repeated, except that the mixture of 297 g. of ethylene glycol monomethyl ether with 54 g of cyanocylohexane recovered in Example 1 and 296 g of cyanocyclohexane (A) were used in place of 300 g of ethylene glycol monomethyl ether and 350 g of cyanocyclohexane (A) (i.e. a total of 297 g of ethylene glycol monomethyl ether and 350 g of cyanocyclohexane was used ). The yield of the produced cyclohexanecarboguanamine and the Hasen color number of the methylolated resin were as shown in Table 2.

EXAMPLE 4

The procedure of Example 1 was repeated, except that cyanocylohexane (D) was used in place of cyanocyclohexane (A), the amount of the dicyandiamide was changed from 243 g to 216 g (2.57 mols: 0.80 mol part per mol part of the charged cyanocyclohexane), and the addition of the dicyandiamide was carried out at a fixed speed (0.2 mol par per hour per mol part of the charged cyanocyclohexane) over a period of 4.0 hours. The yield of the produced cyclohexanecarboguanamine and the Hasen color number of the methylolated resin were as shown in Table 2.

EXAMPLE 5

The procedure of Example 1 was repeated, except that cyanocyclohexane (E) was used in place of the cyanocyclohexane (A), the amount of the dicyandiamide was changed from 243 g to 216 g (2.57 mols: 0.80 mol part per mol part of the charged cyanocyclohexane), and the addition of dicyandiamide was carried out at a fixed speed (0.3 mol part per hour per mol part of the charged cyanocyclohexane) over a period of 2.67 hours. The yield of the produced cyclohexane carboguanamine and the Hasen color number of the metylolated resin were as shown in Table 2.

EXAMPLE 6

The procedure of Example 1 was repeated, except that cyanocylohexane (H) was used in place of the cyanocyclohexane (A), the amount of the dicyandiamide was changed from 243 g to 251 g (2.99 mols: 0.93 mol part per mol part of the charged cyanocyclohexane), and the addition of the. dicyandiamide was carried out at a fixed speed (0.2 mol part per hour per mol part of the charged cyanocyclohexane) over a period of 4.65 hours. The yield of the produced cyclohexanecarboguanamine and the Hasen color number of the methylolated resin were as shown in Table 2.

EXAMPLE 7

The procedure of Example 2 was repeated, except that argon was used in place of nitrogen. The yield of the produced cyclohexanecarboguanamine and the Hasen color number of the methylolated resin were as shown in Table 2.

EXAMPLES 8 to 10

The procedure of Example 2 was repeated, except that ethylene glycol monoisopropyl ether, ethylene glycol monobutyl ether, and n-butanol were used each in place of the ethylene glycol monomethyl ether and cyanocyclohexanes (D), (E), and (H) were each used in place of the cyanocyclohexane (A). The yields of the produced cyclohexanecarboguanamine and the Hasen color numbers of the methylolated resins were as shown in Table 2.

EXAMPLE 11

The procedure of Example 1 was repeated, except that the displacement of the inner gas of the reactor in preparation for the reaction of cyanocyclohexane with dicyandiamide was carried out to an oxygen concentration of 7.0% by volume and the continued flow of nitrogen into the reactor interior was omitted. The yield of the produced cyclohexanecarboguanamine and the Hasen color number of the methylolated resin were as shown in Table 2.

EXAMPLES 12 to 14

The procedure of Example 1 was repeated, except that cyanocyclohexanes (C), (F), and (G) were each used in place of the cyanocylohexane (A). The yields of the produced cyclohexanecarboguanamine and the Hasen color numbers of the methylolated resins were as shown in Table 2.

CONTROL 1

The procedure of Example 1 was repeated, except that the reaction of cyanocyclohexane with dicyandiamide was carried out in the atmosphere of air and cyanocyclohexane (H) was used in place of the cyanocyclohexane (A). The yield of the produced cyclohexanecarboguanamine and the Hasen color number of the methylolated resin were as shown in Table 2.

CONTROL 2

In a four-necked flask having an inner volume of 2 liters and fitted with a thermometer, a stirrer, and a reflux condenser, 300 g of ethyleye glycol monomethyl ether, 350 g (3.21 mols) of cyanocyclohexane (B), 270 g of dicyandiamide (3.21 mols: 1 mol part per mol part of the charged cyanocyclohexane), and 9.0 g (0.16 mol) of potassium hydroxide were placed and, with the interior of the flask displaced several times with nitrogen to lower the oxygen concentration in the inner gas of the flask below 2.5% by volume stirred and heated to the level of reflux (145° C.) under continued supply of nitrogen. Then, the stirring of the reaction mixture was continued further for 5 hours under the reflux condition and then cooled to 100° C. The reaction solution was transferred into a kneader having an inner volume of 2 liters and heated under a vacuum to recover a mixture of 297 g of ethylene glycol monomethyl ether and 235 g of unaltered cyanocyclohexane.

The slightly yellow solid substance consequently obtained and 370 ml of water added thereto were stirred and heated to 90° C. The resulant mixture was filtered and the solid substance obtained by the filtration was dried. The solid substance thus produced contained 182 g of cyclohexanecarboguanamine and 42 g of melamine. The yield of the produced cyclohexanecarboguanamine and the Hasen color number of the methylolated resin were as shown in Table 2.

TABLE 2

| Example | Cyanocyclo-hexane | Oxygen concen-tration (% by volume) | Dicyandiamide Ratio (1) | Speed of addition (2) | Yield (mol %) based on Cyanocyclo-hexane | Dicyandiamine | Hasen color index of methylolated resin |
| --- | --- | --- | --- | --- | --- | --- | --- |
| 1 | A | <2.5 | 0.9 | 0.2 | 99.0 | 93.0 | 60 |
| 2 | B | <2.5 | 0.9 | 0.2 | 98.9 | 93.1 | 60 |
| 3 | (3) | <2.5 | 0.9 | 0.2 | 99.0 | 93.0 | 50 |
| 4 | D | <2.5 | 0.8 | 0.2 | 99.0 | 97.0 | 60 |
| 5 | E | <2.5 | 0.8 | 0.3 | 98.5 | 92.0 | 60 |
| 6 | H | <2.5 | 0.93 | 0.2 | 98.5 | 90.3 | 60 |
| 7 | B | <2.5 | 0.8 | 0.2 | 98.8 | 93.0 | 60 |
| 8 | D | <2.5 | 0.9 | 0.2 | 98.8 | 92.5 | 60 |
| 9 | E | <2.5 | 0.9 | 0.2 | 99.0 | 92.3 | 60 |
| 10 | H | <2.5 | 0.9 | 0.2 | 98.9 | 92.0 | 60 |
| 11 | A | 7.0 | 0.9 | 0.2 | 98.8 | 92.8 | 120 |
| 12 | C | <2.5 | 0.9 | 0.2 | 98.7 | 92.8 | 140 |
| 13 | F | <2.5 | 0.9 | 0.2 | 98.8 | 92.9 | 160 |
| 14 | G | <2.5 | 0.9 | 0.2 | 98.6 | 92.7 | 150 |
| Control |  |  |  |  |  |  |  |
| 1 | H | 21 | 0.9 | 0.2 | 98.5 | 92.8 | 300 |
| 2 | B | <2.5 | 1.0 | — | 89.4 | 29.4 | 60 |

(1) Number of mol part of dicyandiamide per mol part of the charged cyanocyclohexane.
(2) Number of mol part of dicyandiamide added per hour per mol part of the charged cyanocylohexane.
(3) Mixture of cyanocyclohexane recovered in Example 1 with cyanocyclohexane (A).

What is claimed is:

1. In a method for the production of cyclohexanecarboguanamine by the reaction of cyanocyclohexane with dicyandiamide in an organic solvent possessing a hydroxyl group in the molecular unit thereof at a temperature in the range of 90° to 200° C. in the presence of a basic catalyst, the improvement which comprises carrying out said reaction using 0.60 to 0.95 mol of dicyandiamide per mol of in cyanocyclohexane in an atmosphere substantially incapable of producing any effect of oxygen.

2. A method according to claim 1, wherein said atmosphere substantially incapable of producing any effect of oxygen is the atmosphere of at least one inert gas selected from the group consisting of nitrogen and argon.

3. A method according to claim 1, wherein said atmosphere substantially incapable of producing any effect of oxygen has an oxygen concentration of not more than 5% by volume.

4. A method according to claim 1, wherein said dicyandiamide is sequentially added into said organic solvent which contains cyanocyclohexane at a rate of 0.05 to 0.35 mol per hour per mol of cyanocyclohexane.

5. A method according to claim 4, wherein said dicyandiamide is used at a ratio of 0.65 to 0.90 mol to 1 mol of cyanocyclohexane.

6. A method according to claim 4, wherein said dicyandiamide is sequentially added in the form of a mixture suspended and/or dissolved in an organic solvent to the solution of cyanocyclohexane in an organic solvent.

7. A method according to claim 1, wherein said organic solvent is at least one member selected from the group consisting of ethylene glycol monoalkyl ethers represented by the following formula II:

$$ROCH_2CH_2OH \qquad (II)$$

wherein R is an alkyl group of 1 to 4 carbon atoms, and butanols.

8. A method according to claim 7, wherein the reaction temperature is in the range of 110° to 180° C.

9. A method according to claim 7, wherein said basic catalyst is an alkali metal hydroxide or an alkali metal alcoholate.

* * * * *